(12) United States Patent
Guo et al.

(10) Patent No.: US 11,878,082 B2
(45) Date of Patent: Jan. 23, 2024

(54) BIOMASS-BASED ENCAPSULATING MATERIAL FOR PROTECTION OF PROBIOTIC ACTIVITY AND AN ENCAPSULATING METHOD

(71) Applicant: Chengdu bangjialejun Biotechnology Co., Ltd, Chengdu (CN)

(72) Inventors: Junling Guo, Chengdu (CN); Yaoyao Zhang, Chengdu (CN); Jiezhou Pan, Chengdu (CN); Guidong Gong, Chengdu (CN)

(73) Assignee: CHENGDU BANGJIALEJUN BIOTECHNOLOGY CO., LTD, Chengdu (CN)

( * ) Notice: Subject to any disclaimer, the term of this patent is extended or adjusted under 35 U.S.C. 154(b) by 240 days.

(21) Appl. No.: 17/481,263

(22) Filed: Sep. 21, 2021

(65) Prior Publication Data
US 2022/0000793 A1   Jan. 6, 2022

(30) Foreign Application Priority Data
Jul. 8, 2021   (CN) .......................... 202110770726.3

(51) Int. Cl.
  *A61K 9/51*   (2006.01)
  *A61K 35/741*   (2015.01)
  *A61K 9/50*   (2006.01)

(52) U.S. Cl.
  CPC .......... *A61K 9/5176* (2013.01); *A61K 9/5073* (2013.01); *A61K 9/5115* (2013.01); *A61K 9/5169* (2013.01); *A61K 35/741* (2013.01)

(58) Field of Classification Search
  CPC .. A61K 9/5176; A61K 9/5073; A61K 9/5115; A61K 9/5169; A61K 35/741
  See application file for complete search history.

(56) References Cited

FOREIGN PATENT DOCUMENTS

| CN | 108841756 A | 11/2018 |
|---|---|---|
| CN | 110801021 A | 2/2020 |

OTHER PUBLICATIONS

Vikram Singh Raghuwanshi and Gil Garnier, "Cellulose Nano-Films as Bio-Interfaces" in Frontiers in Chemistry Jul. 2019. (Year: 2019).*
Guo et al., CN 108841756 A submitted in form 1449 and using PE2E Eng. Trans. 2018. (Year: 2018).*

* cited by examiner

*Primary Examiner* — Blessing M Fubara
(74) *Attorney, Agent, or Firm* — Best & Flanagan LLP

(57) ABSTRACT

An encapsulated probiotic, an encapsulating layer and a method of encapsulating probiotics are disclosed. The encapsulated probiotic includes an encapsulating layer and probiotics, and the encapsulating layer includes a nano-film having two layers for encapsulating probiotics. A first layer is formed through biological macromolecules and metal ions on surfaces of the probiotics by covalent cross-linking or metal chelating action in situ, and a second layer is formed by interactions between a bio-enzyme and the biological macromolecules. The nano-film formed in situ on cell walls of probiotics is used for encapsulation and protection of probiotics.

8 Claims, 4 Drawing Sheets

BIOMASS-BASED ENCAPSULATING MATERIAL FOR PROTECTION OF PROBIOTIC ACTIVITY AND AN ENCAPSULATING METHOD

BACKGROUND OF THE APPLICATION

Technical Field

The invention relates to the field of biotechnology, in particular, to a biomass-based encapsulating material for protection of probiotic activity and an encapsulating method.

Description of Related Art

Biogroups of enteric microorganisms of human play a critical role of maintaining a healthy gastrointestinal function and other physiological processes, which leads to increasing interest of people using oral microorganisms as treatment and diagnostic methods. However, probiotics are extremely sensitive to external environmental stimulation, for example, to oxygen, temperature and external nutritional level, are low in resistance to a low pH value environment in a digestive tract, and will be inhibited by active free radicals, and in particular, antibacterial agents such as antibiotics will damage probiotics groups severely. Clinically, the most common using scene of probiotics is to maintain balance of intestinal flora by administrating the probiotics, thereby avoiding side effects caused by using antibiotics. However, it is often difficult for the administrated probiotics to endure damage of the antibiotics, such that it is hard to plant the probiotics fixedly. In addition, it is often difficult to maintain the activity of the probiotics in transportation and storage processes.

Therefore, a major problem in development of a probiotics preparation is how to maintain the activity of the probiotics in storage and use. Addition of a protecting agent into the probiotics preparation is a common method at present. For example, an encapsulating technology can provide a relatively proper micro-environment to the probiotics, such that thalli are isolated from a relatively severe external environment, and therefore, the thalli that are quite sensitive and are difficult to store in a normal state can be stored for a long time. However, an existing probiotics encapsulating technology still has the problems of high cost, complex preparation process, relatively low encapsulating rate, relatively poor activity protecting capacity and the like. In particular, an encapsulating technology capable of being used for protecting the probiotics from being damaged by antibiotics has not been reported yet at present.

In existing encapsulating technologies, for example, CN11081021A provides a method for embedding intestinal compound probiotics by using modified pectin; CN104856924B provides a method for preparing an external probiotics microcapsule; and CN111436614A provides a probiotics delivery microcapsule based on shiitake mushroom soluble dietary fibers and a preparation method. Although these encapsulating methods can store the probiotics to a certain extent or enable the probiotics to maintain certain activity under a pH condition of the gastrointestinal tract, its preparation process is complex. Moreover, the activity protecting capacity to the probiotics under a more severe external condition, for example in the presence of antibiotics, has not been researched.

SUMMARY

In view of the problems existing in the prior arts, a biomass-based encapsulating material for protection of probiotic activity and an encapsulating method are provided in the present invention, which has strong activity protection ability and can avoid damages of antibiotics to probiotics.

The technical scheme adopted by the present invention is as below.

A biomass-based encapsulating material for protection of probiotic activity includes a nano-film for encapsulating probiotics. The nano-film includes two layers, wherein a first layer is formed through natural biological macromolecules and metal ions on surfaces of the probiotics by covalent cross-linking or metal chelating action in situ, and a second layer is formed by interactions between a bio-enzyme and the natural biological macromolecules.

Further, the bio-enzyme is one of or a mixture of two or more of β-galactosidase, amylopsin, α-glucosaccharase, β-glucosaccharase, pancreatic lipase, trypsin and cellulase at any proportion.

Further, the metal ions are one of or a mixture of two or more of cations of Al, Fe, Zn, Mn, Ni, Co and V.

Further, the natural biological molecules are one of or a mixture of two or more of natural polyphenol, dopamine and derivatives thereof, polysaccharide biomass and polysaccharide biomass at any proportion.

Further, the probiotics are one of or a mixture of two or more of lactic acid *bacillus, bacillus,* saccharomycetes, *bifidobacterium,* Gram-positive cocci, *Escherichia coli* and photosynthetic bacteria at any proportion.

An encapsulating method for a biomass-based encapsulating material for protection of probiotic activity includes the following steps:

Step S1, mixing a metal salt aqueous solution with a probiotics solution fully, adding a natural biological macromolecular aqueous solution, adjusting a pH value, carrying out a full reaction and carrying out washing to obtain a probiotics solution containing the probiotics coated with the first layer of the nano-film;

Step S2, adjusting the concentration of the probiotics solution containing the probiotics coated by the first layer of the nano-film obtained in the step S1, and repeatedly operating the step S1 for 0-N times; and Step S3, adjusting the concentration of the probiotics solution containing the probiotics coated by the first layer of the nano-film obtained in the step S2, adding a bio-enzyme aqueous solution, carrying out a full reaction to form the probiotics coated with the second layer of the nano-film, and carrying out freeze drying to obtain the encapsulated probiotics.

Further, the pH is adjusted to 7.0 in the step S1 by adopting a sodium hydroxide aqueous solution or a PBS buffer solution.

Further, the concentration of the probiotics solution obtained in the step S1 is $1*10^6$-$1*10^9$ CFU/mL, a concentration of the metal salt aqueous solution is 1-10 mg/mL, a concentration of the natural biological macromolecular aqueous solution is 10-100 mg/mL, a volume ratio of the metal salt aqueous solution to the probiotics solution is 1:50, and a volume ratio of the natural biological macromolecular aqueous solution to the probiotics solution obtained in the step S1 is 1:50.

Further, the concentration of the probiotics solution containing the probiotics coated with the first layer of the nano-film after adjustment in the steps S2 and S3 is $1*10^6$-$1*10^9$ CFU/mL, a concentration of the bio-enzyme aqueous solution in the step S3 is 1-20 mg/mL, and a volume ratio of the bio-enzyme aqueous solution to the probiotics solution containing the probiotics coated with the first layer of the nano-film is 1:50.

Further, a washing process in the step S1 comprises the following sub-steps: adding a PBS buffer solution into a mixed solution, and carrying out centrifugalization after full mixing to remove a supernate; repeating the operation for 1-3 times; and carrying out centrifugalization for 2-5 min by adopting a 1000-5000 g centrifugal force.

The present invention has the following beneficial effects:

(1) The nano-film formed on cell walls of the probiotics in situ is used for encapsulation and protection of the probiotics, and the nano-film composed of natural biomass is low in cost and free of toxic and side effects.

(2) Regardless of being cultured in environments under high concentration antibiotics and active free radicals, the relative activity of encapsulated probiotics is approximate to or even higher than 90%. The relative activity of the unprotected probiotics is lower than 30%, or even completely unable to survive.

(3) According to the encapsulating material of the present invention, the second layer of the nano-film coating the probiotics is formed by combining a bio-enzyme in situ with a first layer of biomass-based material by means of hydrogen bonds, hydrophobic interaction, electrostatic interaction and the like. The second layer can hydrolyze macromolecular nutritional substances such as proteins, cellulose, starch fat and lactose and convert the macromolecular nutritional substances into small molecular nutritional substances that are easily absorbed by the probiotics and human body, thereby promoting fixed planting and reproduction of the probiotics and promoting digestion and absorption of the nutritional substances by a patient.

(4) According to the encapsulating material of the present invention, the nano-film formed on the surface of the probiotics in situ can be bonded with water molecules nearby, and formation of ice crystals can be avoided when the nano-film is frozen, such that damage to the probiotics in the freezing process is avoided.

(5) The encapsulating method of the present invention is simple, thereby facilitating implementation of low cost industrial production. A material for coating is the natural biological material which is very high in safety. The obtained probiotics preparation can maintain very high activity in transportation and storage processes, and therefore, the encapsulating method is suitable for the field of probiotics preparations.

DETAILED DESCRIPTION

Figure 1:
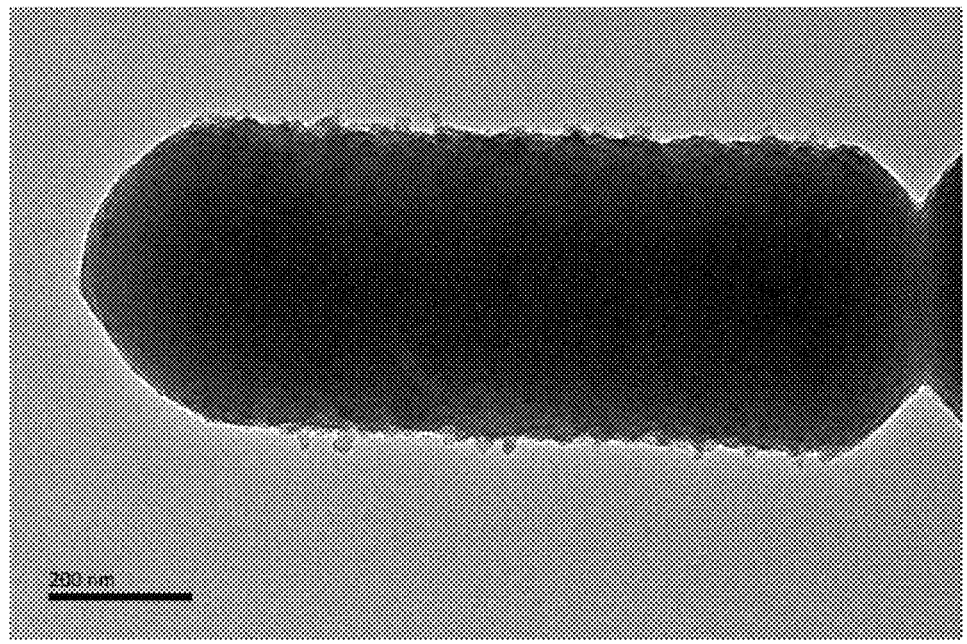
FIG. 1 is a TEM diagram of encapsulating lactic acid bacillus by the biomass-based encapsulating material for protection of probiotic activity obtained in Embodiment 3.

Further description of the present invention will be made below in combination with drawings and specific embodiments.

A biomass-based encapsulating material for protection of probiotic activity includes a nano-film for encapsulating probiotics, the nano-film including two layers, wherein a first layer is formed by natural biological macromolecules and metal ions on surfaces of the probiotics through covalent cross-linking or metal chelating action in situ, and a second layer is formed by interaction between a bio-enzyme and the natural biological macromolecules.

The bio-enzyme is one of or a mixture of two or more of β-galactosidase, amylopsin, α-glucosaccharase, β-glucosaccharase, pancreatic lipase, trypsin and cellulase at any proportion. The metal ions are one of or a mixture of two or more of cations of Al, Fe, Zn, Mn, Ni, Co and V. The metal ions are metal ions that are good in biocompatibility. The natural biological molecules are one of or a mixture of two or more of natural polyphenol, dopamine and derivatives thereof, polysaccharide biomass and polysaccharide biomass at any proportion. The natural macromolecular polyphenol can be bayberry tannin, persimmon tannin, black wattle bark tannin, dahurian larch tannin, tannic acid and the like. The natural small molecular polyphenol can be ellagic acid, epigallocatechin gallate, catechin gallate, anthocyanin, catechin and the like. The polysaccharide biomass is chitosan, carboxymethyl chitosan, cellulose, carboxymethylcellulose, hyaluronic acid and the like. The protein biomass includes, for example, gelatin, collagen and the like. The probiotics are one of or a mixture of two or more of lactic acid *bacillus, bacillus,* saccharomycetes, *bifidobacterium,* Gram-positive cocci, *Escherichia coli* and photosynthetic bacteria at any proportion. Common probiotics include *Bifidobacterium bifidum, Bifidobacterium breve, Bifidobacterium longum, Lactobacillus casei, Lactobacillus acidophilus, Lactobacillus helveticus, Lactobacillus rhamnosus, Lactobacillus plantarum, Lactobacillus lactis, Streptococcus lactis* and *Escherichia coli* Nissle 1917. The encapsulated probiotics can either include one probiotic or include a probiotic flora formed by various different probiotics.

An encapsulating method for a biomass-based encapsulating material for protection of probiotic activity includes the following steps:

Step S1, a metal salt aqueous solution is mixed with a probiotics solution fully, a natural biological macromolecular aqueous solution is added, a pH value adjusted, a full reaction is carried out and washing is carried out to obtain probiotics coated with the first layer of the nano-film.

A concentration of the probiotics solution preferably is $1*10^6$-$1*10^9$ CFU/mL, a concentration of the metal salt solution is preferably 1-10 mg/mL, and a concentration of the natural biological macromolecules is 10-100 mg/mL. A volume ratio of the metal salt aqueous solution to the probiotics solution is 1:50 and the natural biological macromolecular aqueous solution is added according to a volume ratio of the natural biological macromolecular aqueous solution to the probiotics solution of 1:50.

When metal chelation serves as main action to form the nano-film, the metal salt aqueous solution and the probiotics solution are mixed fully, the volume ratio of the metal salt aqueous solution to the probiotics solution is 1:50, the natural biological macromolecular aqueous solution is added to be fully mixed at a volume ratio of the metal salt aqueous solution to the probiotics solution of 1:50, and the sodium hydroxide aqueous solution is added to adjust the pH value of the solution. The metal ions are complexed with catechol or carboxyl with natural biological macromolecules to form a supermolecular nano-film to coat the probiotics. When covalent binding serves as main action to form the nano-film, the probiotics solution and the natural biological macromolecular aqueous solution are fully mixed, the PBS buffer solution is added to adjust the pH value, and they are fully mixed. Catechol is crosslinked on the surfaces of cell walls of probiotics to form the nano-film.

The washing process is as follows.

The PBS buffer solution is added into the mixed solution after a reaction, the PBS buffer solution and the mixed solution are fully mixed and centrifugalized to remove a supernate, and then the operation is repeated for 1-3 times. Centrifugalization is carried out for 2-5 min by adopting 1000-5000 g centrifugal force. A concentration of the buffer solution is 0.05-0.5 mol/L.

Step S2, a concentration of probiotics solution containing probiotics coated by the supermolecular nano-film (i.e., the first layer of the nano-film) obtained in the step S1 is adjusted, and the step S1 is repeatedly operated for 0-N times, N being 3. Repeated operation further coats the probiotics coated with the supermolecular nano-film obtained in the step S1.

Step S3, a concentration of probiotics solution containing probiotics coated by the supermolecular nano-film (i.e., the first layer of the nano-film) obtained in the step S2 is adjusted, a bio-enzyme aqueous solution is added, a volume ratio of the bio-enzyme aqueous solution to the probiotics solution being 1:50, carrying out a full reaction to form probiotics coated with the second layer of nano-film, and carrying out freeze drying to obtain the encapsulated probiotics. A concentration of the bio-enzyme aqueous solution is 1-20 mg/mL. The bio-enzyme and the nano-film formed on the probiotics in the step S2 form the second layer of nano-film via hydrophobic interaction and multiple interactions such as hydrogen bonds and electrostatic interaction.

Embodiment 1

A biomass-based encapsulating material for protection of probiotic activity is prepared by the following steps.

Step S1, 1 mL of an *E coli* Nissle (*Escherichia coli* Nissle) suspension with a concentration of $1*10^8$ CFU/mL is taken, the *E coli* Nissle suspension is centrifugalized for 3 min by a 3000 g of centrifugal force, a supernate is removed, then operations of centrifugalizing and removing the supernate are repeated for 3 times, then 0.05 mol/L PBS is added again to adjust the total volume to 500 μL, and they are mixed uniformly to obtain a probiotics solution. 5 μL of a $FeCl_3$ aqueous solution with a concentration of 10 mg/mL is added into the probiotics solution, vortex oscillation is carried out for 10 s to mix the two fully, then 5 μL of a tannic acid aqueous solution with a concentration of 40 mg/mL is added, and vortex oscillation is carried out for 10 s to mix them fully. Fe3+ ions are complexed with hydroxyl of tannic acid to form a supermolecular nano-film to coat the probiotics.

500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S2, the concentration of the probiotics solution containing the probiotics coated with the supermolecular nano-film obtained in the previous step, the concentration of the *E coli* Nissle is $1*10^8$ CFU/mL, 1 mL of the solution is taken and 5 μL of $FeCl_3$ aqueous solution with a concentration of 10 mg/mL is added into the solution, and vortex oscillation is carried out for 10 s to mix the two fully. 5 μL of the tannic acid aqueous solution with a concentration of 40 mg/mL is added into the solution, vortex oscillation is carried out for 10 s to mix them fully. $Fe^{3+}$ ions are complexed with hydroxy of tannic acid to form a supermolecular nano-film to continuously coat the probiotics coated with the supermolecular nano-film.

500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S3, the concentration of the probiotics solution containing probiotics coated with the supermolecular nano-film obtained in the step S2 is adjusted, the concentration of the *E coli* Nissle is $1*10^8$ CFU/mL, 1 mL of the solution is taken and 100 μL of a β-galactosidase solution with a concentration of 5 mg/mL is added into the solution. Vortex oscillation is carried out for 10 s to mix them fully, the solution is left to stand for 60 min, and the solution is centrifugalized for 3 min by a 3000 g of centrifugal force to remove a supernate. Freeze drying is carried out on the probiotics coated with the supermolecular nano-film to obtain the encapsulated *E coli* Nissle.

Influence of different antibiotics on activities of the encapsulated *Escherichia coli* Nissle and unencapsulated *Escherichia coli* Nissle of this embodiment is tested.

*Escherichia coli* Nissle is prepared into solutions with a concentration of $1*10^6$ CFU/mL with deionized water, and 6 solutions are prepared and marked as #1-#6 solutions. A ciprofloxacin solution is added into the #1 solution till a final concentration reaches the minimum sterilizing concentration for the antibiotics, the ciprofloxacin solution and the #1 solution are fully mixed and are reacted for 24 hours under a condition of a temperature of 37° C. and a rotating speed of 150 rpm, 100 μL of a bacteria solution is diluted in gradient, and cell activity is evaluated by a spread plate. Tobramycin, neomycin, norfloxacin, levofloxacin and gentamicin solutions are prepared by the same method, and relative cell activities are tested respectively.

(2) Unencapsulated *Escherichia coli* Nissle is prepared into solutions with a concentration of $1*10^6$ CFU/mL with deionized water, and 6 solutions are prepared and marked as

7-#12 solutions. The tobramycin, neomycin, norfloxacin, levofloxacin and gentamicin solutions are respectively added into the #7-#12 solutions according to antibiotic concentration in the step (1) of this embodiment, and then the relative cell activities are tested respectively according to operations in the step (1) of this embodiment.

Figure 3:
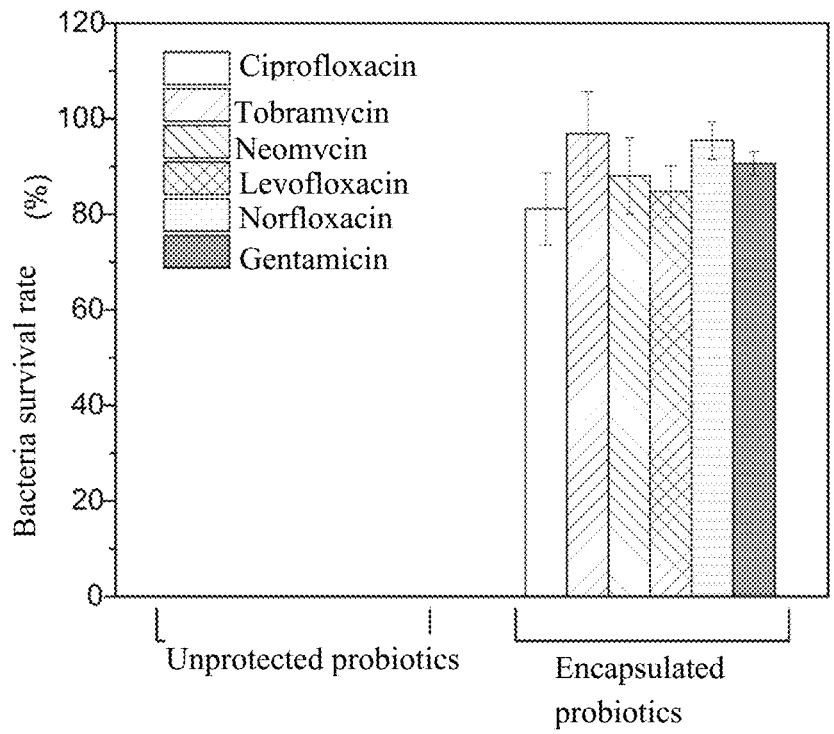
FIG. 3 is a tolerance experimental result of the biomass-based encapsulating material for protection of probiotic activity obtained in Embodiment 1 encapsulating *Escherichia coli* and unprotected *Escherichia coli* on six antibiotics.

A test result is as shown in a table 3. It can be seen from FIG. 3 that in the presence of antibiotics, the unprotected probiotics cannot survive completely and the encapsulated *Escherichia coli* Nissle can keep activities over 80% under action of various antibiotics.

Embodiment 2

A biomass-based encapsulating material for protection of probiotic activity is prepared by the following steps.

Step S1, 1 mL of a *B bifidum* (probitoics *Bifidobacterium bifidum*) suspension with a concentration of $1*10^8$ CFU/mL is taken, the *B bifidum* suspension is centrifugalized for 3 min by a 3000 g of centrifugal force, a supernate is removed, then operations of centrifugalizing and removing the supernate are repeated for 3 times, then 0.05 mol/L PBS is added again to adjust the total volume to 500 μL, and they are mixed uniformly to obtain a probiotics solution. 5 μL of a $FeCl_3$ aqueous solution with a concentration of 10 mg/mL is added into the probiotics solution, vortex oscillation is carried out for 10 s to mix the two fully, then 5 μL of a tannic acid aqueous solution with a concentration of 40 mg/mL is added, and vortex oscillation is carried out for 10 s to mix them fully. $Fe^{3+}$ ions are complexed with hydroxy of tannic acid to form a supermolecular nano-film to continuously coat the probiotics.

Then, 500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S2, the concentration of the probiotics solution containing the probiotics coated with the supermolecular nano-film (i.e., the first layer of nano-film) obtained in the step S1 is adjusted, the concentration of the *B bifidum* is $1*10^8$ CFU/mL, 1 mL of the solution is taken and 100 μL of a pancreatic lipase solution with a concentration of 6 mg/mL is added into the solution. Vortex oscillation is carried out for 10 s to mix them fully, the solution is left to stand for 120 min, and the solution is centrifugalized for 3 min by a 3000 g of centrifugal force to remove a supernate. Unreacted raw materials are washed and removed. Freeze drying is carried out on the probiotics coated with the supermolecular nano-film to obtain the encapsulated *B bifidum*.

Embodiment 3

A biomass-based encapsulating material for protection of probiotic activity is prepared by the following steps.

Step S1, 1 mL of an *L casei* (probitoics *Lactobacillus casei*) suspension with a concentration of $1*10^8$ CFU/mL is taken, the *L casei* suspension is centrifugalized for 3 min by a 3000 g of centrifugal force, a supernate is removed, then operations of centrifugalizing and removing the supernate are repeated for 3 times, then 0.05 mol/L PBS is added again to adjust the total volume to 500 μL, and they are mixed uniformly to obtain a probiotics solution. 5 μL of a $FeCl_3$ aqueous solution with a concentration of 10 mg/mL is added into the probiotics solution, vortex oscillation is carried out for 10 s to mix the two fully, then 5 μL of a tannic acid aqueous solution with a concentration of 40 mg/mL is added, and vortex oscillation is carried out for 10 s to mix them fully. $Fe^{3+}$ ions are complexed with hydroxy of tannic acid to form a supermolecular nano-film to continuously coat the probiotics.

Then, 500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S2, the concentration of the probiotics solution containing the probiotics coated with the supermolecular nano-film (i.e., the first layer of nano-film) obtained in the step S1 is adjusted, the concentration of the *L casei* is $1*10^8$ CFU/mL, 1 mL of the solution is taken and 100 μL of a trypsin solution with a concentration of 10 mg/mL is added into the solution. Vortex oscillation is carried out for 10 s to mix them fully, the solution is left to stand for 60 min, and the solution is centrifugalized for 3 min by a 3000 g of centrifugal force to remove a supernate. Unreacted raw materials are washed and removed. Freeze drying is carried out on the probiotics coated with the supermolecular nano-film to obtain the encapsulated *L casei*.

The encapsulated *L casei* obtained by freeze drying is tested by transmission electron microscope, and a result is shown in FIG. 1. In the figure, an encapsulating material on the surfaces of bacteria can be observed apparently.

(1) The encapsulated *Lactobacillus casei* is prepared into a solution with a concentration of $1*10^6$ CFU/mL with deionized water. 6 solutions are prepared and marked as #1-#6 solutions. A ciprofloxacin solution is added into the #1 solution till a final concentration reaches the minimum sterilizing concentration for the antibiotics, the ciprofloxacin solution and the #1 solution are fully mixed and are reacted for 24 hours under a condition of a temperature of 37° C. and a rotating speed of 150 rpm, 100 μL of a bacteria solution is diluted in gradient, and cell activity is evaluated by a spread plate. Tobramycin, neomycin, norfloxacin, levofloxacin and gentamicin solutions are prepared by the same method, and relative cell activities are tested respectively.

(2) The unencapsulated *Lactobacillus casei* is prepared into a solution with a concentration of $1*10^6$ CFU/mL with deionized water. 6 solutions are prepared and marked as #7-#12 solutions. The tobramycin, neomycin, norfloxacin, levofloxacin and gentamicin solutions are respectively added into the #7-#12 solutions according to antibiotic concentration in the step (1). The relative cell activities are tested respectively according to operations in the step (1).

Figure 4:
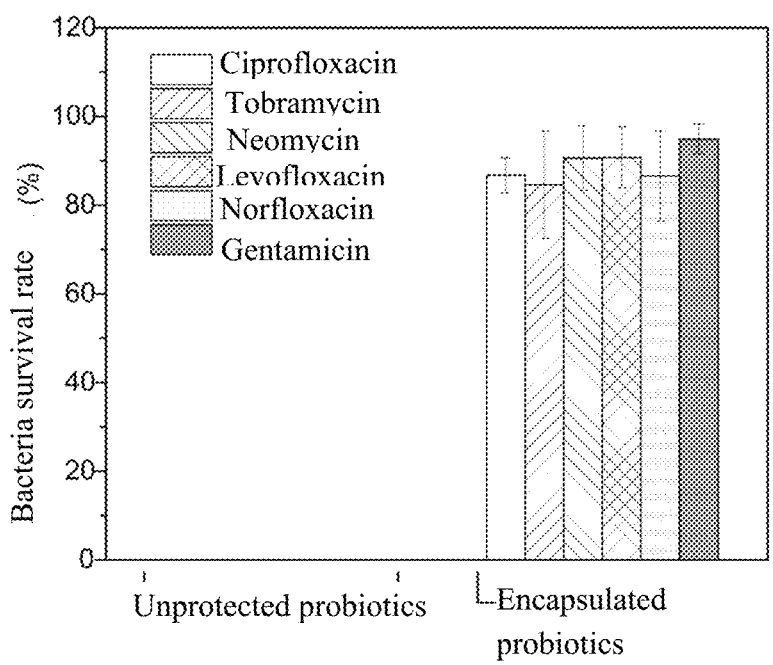
FIG. 4 is a tolerance experimental result of the biomass-based encapsulating material for protection of probiotic activity obtained in Embodiment 3 encapsulating lactic acid bacillus and lactic acid bacillus that is not protected on six antibiotics.

A test result is as shown in a table 4. It can be seen from FIG. 4 that in the presence of antibiotics, the unprotected probiotics cannot survive completely and the encapsulated *Lactobacillus casei* can keep activities over 80% under action of various antibiotics.

Embodiment 4

A biomass-based encapsulating material for protection of probiotic activity is prepared by the following steps.

Step S1, 1 mL of an *S lactis* (probitoics *Streptococcus lactis*) suspension with a concentration of $1*10^8$ CFU/mL is taken, the *L casei* suspension is centrifugalized for 3 min by a 3000 g of centrifugal force, a supernate is removed, then operations of centrifugalizing and removing the supernate are repeated for 3 times, then 0.05 mol/L PBS is added again to adjust the total volume to 500 μL, and they are mixed uniformly to obtain a probiotics solution. 5 μL of a $FeCl_3$ aqueous solution with a concentration of 10 mg/mL is added into the probiotics solution, vortex oscillation is carried out for 10 s to mix the two fully, then 5 μL of a tannic acid aqueous solution with a concentration of 40 mg/mL is added, and vortex oscillation is carried out for 10 s to mix them fully. $Fe^{3+}$ ions are complexed with hydroxy of tannic acid to form a supermolecular nano-film to continuously coat the probiotics.

Then, 500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S2, the concentration of the probiotics solution containing the probiotics coated with the supermolecular nano-film (i.e., the first layer of nano-film) obtained in the step S1 is adjusted, the concentration of the *S lactis* is $1*10^8$ CFU/mL, 1 mL of the solution is taken and 100 μL of a β-galactase solution with a concentration of 5 mg/mL is added into the solution. Vortex oscillation is carried out for 10 s to mix them fully, the solution is left to stand for 60 min, and the solution is centrifugalized for 3 min by a 3000 g of centrifugal force to remove a supernate. Unreacted raw materials are washed and removed. Freeze drying is carried out on the probiotics coated with the supermolecular nano-film to obtain the encapsulated *S lactis*.

Embodiment 5

A biomass-based encapsulating material for protection of probiotic activity is prepared by the following steps.

Step S1, 1 mL of a probiotics flora solution (including *Lactobacillus casei, Lactobacillus acidophilus, Lactobacillus helveticus, Lactobacillus rhamnosus, Lactobacillus plantarum, Lactobacillus lactis* and *Escherichia coli* Nissle, and the probiotics are formed by being mixed at any proportion) suspension with a concentration of $1*10^8$ CFU/mL is taken, the probiotics flora suspension is centrifugalized for 3 min by a 3000 g of centrifugal force, a supernate is removed, then operations of centrifugalizing and removing the supernate are repeated for 3 times, then 0.05 mol/L PBS is added again to adjust the total volume to 500 μL, and they are mixed uniformly to obtain a probiotics solution. 5 μL of a $FeCl_3$ aqueous solution with a concentration of 10 mg/mL is added into the probiotics solution, vortex oscillation is carried out for 10 s to mix the two fully. Then 5 μL of a tannic acid aqueous solution with a concentration of 40 mg/mL is added, and vortex oscillation is carried out for 10 s to mix them fully. $Fe^{3+}$ ions are complexed with hydroxy of tannic acid to form a supermolecular nano-film to continuously coat the probiotics.

Then, 500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S2, the concentration of the probiotics flora solution containing the probiotics coated with the supermolecular nano-film (i.e., the first layer of nano-film) obtained in the step S1 is adjusted, the concentration of the probiotics flora solution is $1*10^8$ CFU/mL, 1 mL of the solution is taken and 100 μL of an enzyme mixed solution (including β-galactosidase, amylopsin, α-glucosidase, β-glucosidase, pancreatic lipase, trypsin and cellulase, and the enzymes are formed by being mixed at any proportion) with a concentration of 5 mg/mL is added into the solution. Vortex oscillation is carried out for 10 s to mix them fully, the solution is left to stand for 120 min, and the solution is centrifugalized for 3 min by a 3000 g of centrifugal force to remove a supernate. Unreacted raw materials are washed and removed. Freeze drying is carried out on the probiotics coated with the supermolecular nano-film to obtain the encapsulated probiotics flora.

Figure 2:
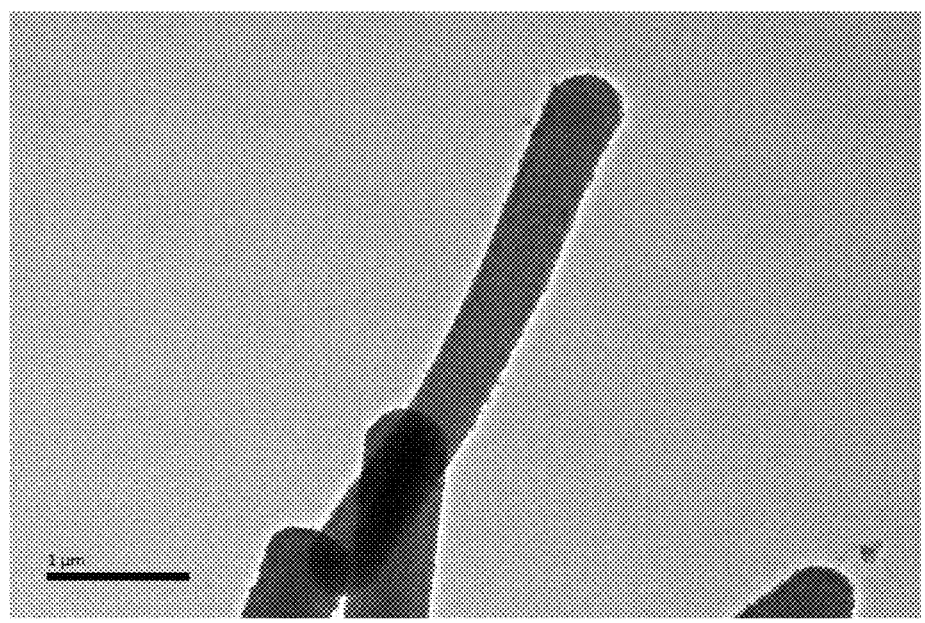
FIG. 2 is a TEM diagram of encapsulating a probiotics mixture by the biomass-based encapsulating material for protection of probiotic activity obtained in Embodiment 5.

The encapsulated probiotics flora obtained by freeze drying is tested by transmission electron microscope, and a result is shown in FIG. 2. In the FIG. 2, an encapsulating material on the surfaces of bacteria can be observed apparently.

(1) A probiotics mixture obtained in this embodiment is prepared into solutions with a concentration of $1*10^6$ CFU/mL with deionized water, and 6 solutions are prepared and marked as #1-#6 solutions. A ciprofloxacin solution is added into the #1 solution till a final concentration reaches the minimum sterilizing concentration for the antibiotics, the ciprofloxacin solution and the #1 solution are fully mixed and are reacted for 24 hours under a condition of a temperature of 37° C. A rotating speed of 150 rpm, 100 μL of a bacteria solution is diluted in gradient, and cell activity is evaluated by a spread plate. Tobramycin, neomycin, norfloxacin, levofloxacin and gentamicin solutions are prepared by the same method, and relative cell activities are tested respectively.

(2) Unencapsulated probiotics mixture is prepared into solutions with a concentration of $1*10^6$ CFU/mL with deionized water, and 6 solutions are prepared and marked as #7-#12 solutions. The tobramycin, neomycin, norfloxacin, levofloxacin and gentamicin solutions are respectively added into the #7-#12 solutions according to antibiotic concentration in the step (1) of this embodiment, and then the relative cell activities are tested respectively according to operations in the step (1) of this embodiment.

Figure 5:
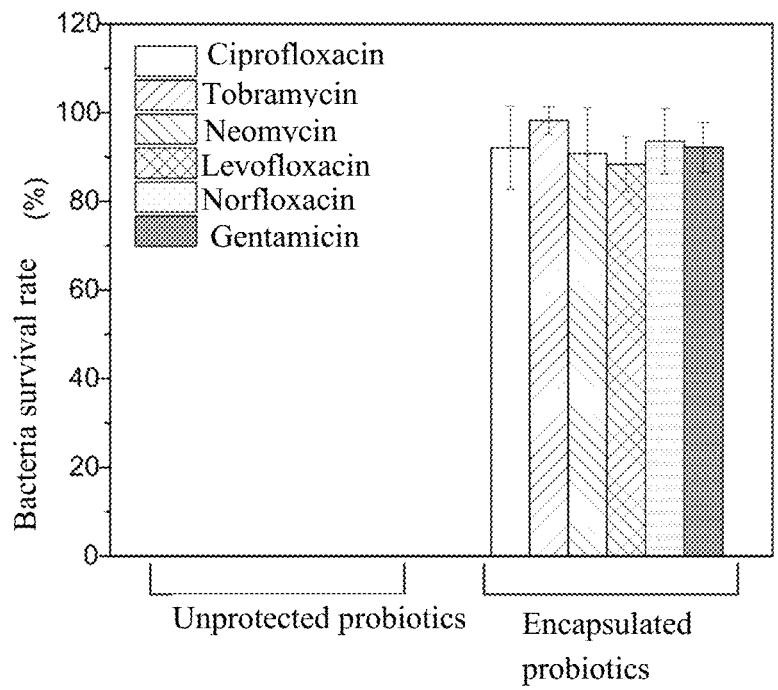
FIG. 5 is a tolerance experimental result of the biomass-based encapsulating material for protection of probiotic activity obtained in Embodiment 5 encapsulating probiotics mixture and probiotics mixture that is not protected on six antibiotics.

As shown in the table 5, it can be seen from FIG. 5 that in the presence of antibiotics, the unprotected probiotics cannot survive completely and the encapsulated probiotics mixture can keep activities over 80% under action of various antibiotics.

Embodiment 6

A biomass-based encapsulating material for protection of probiotic activity is prepared by the following steps.

Step S1, 1 mL of an *E coli* Nissle (probitoics *Escherichia coli* Nissle) suspension with a concentration of $1*10^8$ CFU/mL is taken, the *L casei* suspension is centrifugalized for 3 min by a 3000 g of centrifugal force, a supernate is removed, then operations of centrifugalizing and removing the supernate are repeated for 3 times, then 0.05 mol/L PBS is added again to adjust the total volume to 500 μL, and they are mixed uniformly to obtain a probiotics solution. 5 μL of a $FeCl_3$ aqueous solution with a concentration of 10 mg/mL is added into the probiotics solution, vortex oscillation is carried out for 10 s to mix the two fully, then 5 μL of a tannic acid aqueous solution with a concentration of 40 mg/mL is added, and vortex oscillation is carried out for 10 s to mix them fully. $Fe^{3+}$ ions are complexed with hydroxy of tannic acid to form a supermolecular nano-film to continuously coat the probiotics.

Then, 500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S2, the concentration of the probiotics solution containing the probiotics coated with the supermolecular nano-film obtained in the previous step, the concentration of the *E coli* Nissle is $1*10^8$ CFU/mL, 1 mL of the solution is taken and 5 μL of $FeCl_3$ aqueous solution with a concentration of 10 g/mL is added into the solution, and vortex oscillation is carried out for 10 s to mix the two fully. 5 μL of the tannic acid aqueous solution with a concentration of 40 mg/mL is added into the solution, vortex oscillation is carried out for 10 s to mix them fully. Fe3+ ions are complexed with hydroxy of tannic acid to form a supermolecular nano-film to continuously coat the probiotics coated with the supermolecular nano-film.

500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S3, the concentration of the probiotics solution containing the probiotics coated with the supermolecular nano-film (i.e., the first layer of nano-film) obtained in the step S2 is adjusted, the concentration of the *E coli* Nissle is $1*10^8$ CFU/mL, 1 mL of the solution is taken and 50 μL of an amylopsin solution with a concentration of 10 mg/mL and 50 μL of α-glucosidase solution with a concentration of 10 mg/mL are added into the solution. Vortex oscillation is carried out for 10 s to mix them fully, the solution is left to stand for 60 min, and the solution is centrifugalized for 3 min by a 3000 g of centrifugal force to remove a supernate. Freeze drying is carried out on the probiotics coated with the supermolecular nano-film to obtain the encapsulated *E coli* Nissle.

Influence of different antibiotics on activities of the encapsulated *Lactobacillus casei* and unencapsulated *Lactobacillus casei* of this embodiment is tested.

(1) The encapsulated *Escherichia coli* Nissle is prepared into solutions with a concentration of $1*10^6$ CFU/mL with deionized water. A hydrogen peroxide solution is added into the solution till a final concentration reaches 3%, the hydrogen peroxide solution and the solution are fully mixed and are reacted for 24 hours under a condition of a temperature of 37° C. and a rotating speed of 150 rpm, 100 μL of a bacteria solution is diluted in gradient, and cell activity is evaluated by a spread plate.

(2) Unencapsulated *Escherichia coli* Nissle is prepared into solutions with a concentration of $1*10^6$ CFU/mL with deionized water. Hydrogen peroxide is added according to hydrogen peroxide concentration in the step (1) of this embodiment, and then the relative cell activities are tested respectively according to operations in the step (1) of this embodiment.

Figure 6:
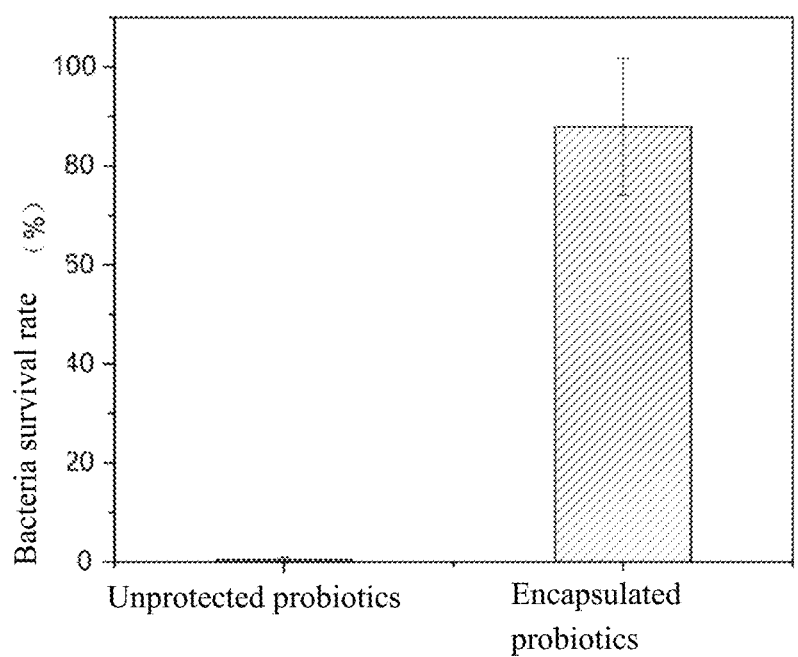
FIG. 6 is a cytotoxicity experimental result of the biomass-based encapsulating material for protection of probiotic activity obtained in Embodiment 6.

A test result is as shown in FIG. 6 and it can be seen from FIG. 6 that treated by hydrogen peroxide, the unprotected probiotics almost completely loses its activity and the encapsulated probiotics can resist damage of hydrogen peroxide and keeps the activity at over 80%.

Influence of freezing on activities of the encapsulated *Escherichia coli* Nissle and unencapsulated *Lactobacillus casei* of this embodiment is tested.

(1) The encapsulated *Escherichia coli* Nissle is prepared into solutions with a concentration of $1*10^6$ CFU/mL with deionized water and are then placed quickly to a −80° C. refrigerator to be frozen for 7 days. Then, the solutions are unfrozen at 37° C., and 100 μL of a bacteria solution is diluted in gradient, and cell activity is evaluated by a spread plate.

(2) Unencapsulated *Escherichia coli* Nissle is prepared into solutions with a concentration of $1*10^6$ CFU/mL with deionized water. The solutions are frozen for 7 days according to the step (1) of this embodiment, and then the relative cell activities are tested respectively according to operations in the step (1) of this embodiment.

Figure 7:
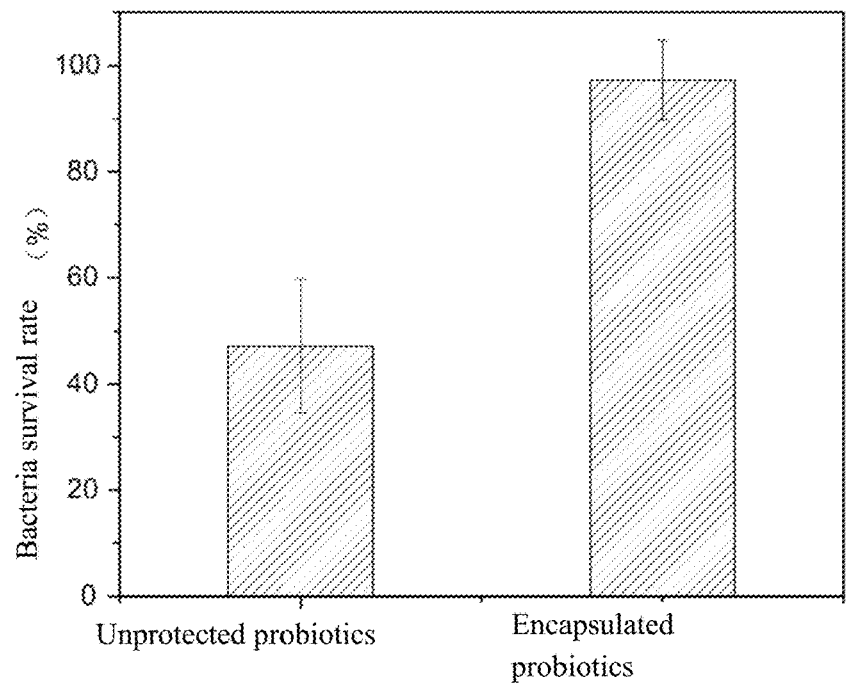
FIG. 7 is a tolerance experimental result of the biomass-based encapsulating material for protection of probiotic activity obtained in Embodiment 6 encapsulating *Escherichia coli* and unprotected *Escherichia coli* on hydrogen peroxide solution.

A test result is as shown in a table 7. It can be seen from FIG. 7 that the activity of the unprotected probiotics after freezing treatment is reduced greatly, and the activity of the encapsulated probiotics after freezing treatment can be completely maintained.

Embodiment 7

A biomass-based encapsulating material for protection of probiotic activity is prepared by the following steps.

Step S1, 1 mL of an *E coli* Nissle (probitoics *Escherichia coli* Nissle) suspension with a concentration of $1*10^8$ CFU/mL is taken, the *L casei* suspension is centrifugalized for 3 min by a 3000 g of centrifugal force, a supernate is removed, then operations of centrifugalizing and removing the supernate are repeated for 3 times, then 0.05 mol/L PBS is added again to adjust the total volume to 500 μL, and they are mixed uniformly to obtain a probiotics solution. 5 μL of a $FeCl_3$ aqueous solution with a concentration of 10 mg/mL is added into the probiotics solution, vortex oscillation is carried out for 10 s to mix the two fully, then 5 μL of an acacia mearnsii tannic acid aqueous solution with a concentration of 40 mg/mL is added, and vortex oscillation is carried out for 10 s to mix them fully. $Fe^{3+}$ ions are complexed with hydroxy of acacia mearnsii tannn to form a supermolecular nano-film to coat the probiotics.

Then, 500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S2, the concentration of the probiotics solution containing the probiotics coated with the supermolecular nano-film obtained in the previous step, the concentration of the *E coli* Nissle is $1*10^8$ CFU/mL, 1 mL of the solution is taken and 5 μL of $FeCl_3$ aqueous solution with a concentration of 10 mg/mL is added into the solution, and vortex oscillation is carried out for 10 s to mix the two fully. Then, 5 μL of the tannic acid aqueous solution with a concentration of 40 mg/mL is added into the solution, vortex oscillation is carried out for 10 s to mix them fully. $Fe^{3+}$ ions are complexed with hydroxy of acacia mearnsii tannin to form a supermolecular nano-film to continuously coat the probiotics coated with the supermolecular nano-film.

500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S3, the concentration of the probiotics solution containing the probiotics coated with the supermolecular nano-film (i.e., the first layer of nano-film) obtained in the step S2 is adjusted, the concentration of the E coli Nissle is $1*10^8$ CFU/mL, 1 mL of the solution is taken and 100 μL of a cellulase solution with a concentration of 6 mg/mL is added into the solution. Vortex oscillation is carried out for 10 s to mix them fully, the solution is left to stand for 60 min, and the solution is centrifugalized for 3 min by a 3000 g of centrifugal force to remove a supernate. Freeze drying is carried out on the probiotics coated with the supermolecular nano-film to obtain the encapsulated E coli Nissle.

Embodiment 8

A biomass-based encapsulating material for protection of probiotic activity is prepared by the following steps.

Step S1, 1 mL of an E coli Nissle (probitoics Escherichia coli Nissle) suspension with a concentration of $1*10^8$ CFU/mL is taken, the L casei suspension is centrifugalized for 3 min by a 3000 g of centrifugal force, a supernate is removed, then operations of centrifugalizing and removing the supernate are repeated for 3 times, then 0.05 mol/L PBS is added again to adjust the total volume to 500 μL, and they are mixed uniformly to obtain a probiotics solution. 5 μL of a $FeCl_3$ aqueous solution with a concentration of 10 mg/mL is added into the probiotics solution, vortex oscillation is carried out for 10 s to mix the two fully, then 5 μL of an epigallocatechin gallate aqueous solution with a concentration of 4 mg/mL is added, and vortex oscillation is carried out for 10 s to mix them fully. $Fe^{3+}$ ions are complexed with hydroxy of epigallocatechin gallate to form a supermolecular nano-film to coat the probiotics.

Then, 500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S2, the concentration of the probiotics solution containing the probiotics coated with the supermolecular nano-film obtained in the previous step, the concentration of the E coli Nissle is $1*10^8$ CFU/mL, 1 mL of the solution is taken and 5 μL of $FeCl_3$ aqueous solution with a concentration of 10 mg/mL is added into the solution, and vortex oscillation is carried out for 10 s to mix the two fully. 5 μL of the epigallocatechin gallate aqueous solution with a concentration of 4 mg/mL is added into the solution, vortex oscillation is carried out for 10 s to mix them fully. $Fe^{3+}$ ions are complexed with hydroxy of epigallocatechin gallate to form a supermolecular nano-film to continuously coat the probiotics coated with the supermolecular nano-film.

500 μL of PBS buffer solution with a concentration of 0.1 mol/L is added into the mixed solution formed by full mixing, and vortex oscillation is carried out for 10 s to mix them fully. The solution is centrifugalized for 3 min by a 3000 g of centrifugal force to remove a supernate. Then the PBS buffer solution is added repeatedly, and operations of mixing, centrifugalizing and removing the supernatant are carried out once; and unreacted raw materials are washed and removed.

Step S3, the concentration of the probiotics solution containing the probiotics coated with the supermolecular nano-film (i.e., the first layer of nano-film) obtained in the step S2 is adjusted, the concentration of the E coli Nissle is $1*10^8$ CFU/mL, 1 mL of the solution is taken and 50 μL of a α-glucosidase solution with a concentration of 10 mg/mL is added into the solution. Vortex oscillation is carried out for 10 s to mix them fully, the solution is left to stand for 60 min, and the solution is centrifugalized for 3 min by a 3000 g of centrifugal force to remove a supernate. Freeze drying is carried out on the probiotics coated with the supermolecular nano-film to obtain the encapsulated E coli Nissle.

The cytotoxicity is tested by adopting the encapsulating material prepared by this embodiment.

Mouse fibroblast cells are inoculated to a 6-pore plate ($3*10^5$ cell/well), are cultured for 24 hours, and are co-cultured for 24 hours by using 100 μg/mL encapsulating material. An FITC Annex in V apoptosis detection kit (BD Biosciences, San Jose, CA, USA) is used, and cell apoptosis is detected according to a description of a manufacturer. Fluorescence intensity is measured by using flow cytometry.

Figure 8:
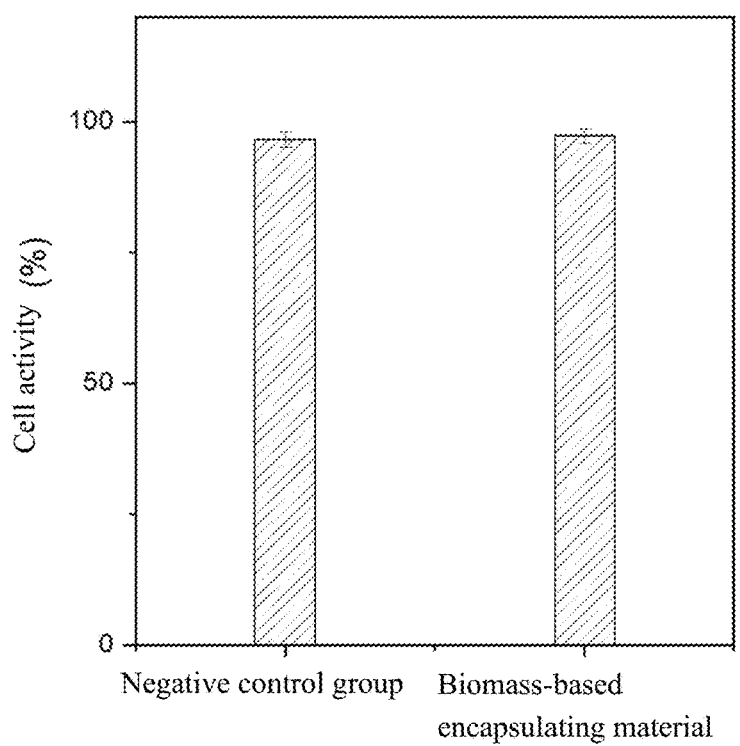
FIG. 8 is a revival activity experimental result of the biomass-based encapsulating material for protection of probiotic activity obtained in Embodiment 8 encapsulating *Escherichia coli* and unprotected *Escherichia coli* after being frozen.

A test result is as shown in FIG. 8 and it can be seen from FIG. 8 that the encapsulating material provided by the present invention has good biocompatibility.

A layer of nano-film is formed in situ on the surfaces of cell walls of the probiotics by means of covalent binding or metal chelation, such that unicellular modification on the probiotics or the probiotics flora can be realized. Then, based on the nano-film, a layer of enzyme-based nano-film is further coated by means of multiple interactions between the bio-enzyme and the first layer of biomass-based material. The formed probiotics nano-film can maintain biological activity and provide a layer of protection to shield external stimulation such as antibiotics and active free radicals. Meanwhile, the nutritional substances can penetrate without affecting activity of the probiotics, and the probiotics are prevented from being killed in the environment, such that it is ensured that the probiotics can grow normally after external sterilizing substances are metabolized. According to the nano-film, ice crystals on the surface of the nano-film are prevented from being formed in a freezing process of the probiotics, such that inactivation of the probiotics in the process of preparing probiotics freeze-dried powder is avoided.

The second layer is the nano-film formed by bonding the bio-enzyme and the natural macromolecules in the first layer via multiple intermolecular interactions (multiple interactions such as hydrogen bonds, hydrophobic interaction and electrostatic interaction in situ by the bio-enzyme), the bio-enzyme on the nano-film can hydrolyze macromolecular nutritional substances such as proteins, cellulose, starch fat and lactose and convert the macromolecular nutritional substances into small molecular nutritional substances that are easily absorbed by the probiotics and human body, thereby promoting fixed planting and reproduction of the probiotics and promoting digestion and absorption of the nutritional substances by a patient.

Regardless of being cultured in an environment with high concentration antibiotics and active free radicals, the relative activity of the encapsulated probiotics by the biomass-based encapsulating material for protection of probiotic activity can be approximate to or even higher than 90%. The relative activity of the probiotics that are not protected is lower than 30%, and even, the probiotics cannot survive completely. Both the active free radicals and antibiotics are molecules with extremely small relative molecular weights. As the substances are hardly intercepted by a conventional encapsulating technology, the activity of the probiotics is hardly protected under an environment of the antibiotics. The biomass-based encapsulating material for protection of probiotic activity can generate multiple interactions based on polyphenol groups and generate relatively strong interactions with various antibiotics to adsorb small molecular medicines near the encapsulating material, thereby avoiding damage of the medicines to the probiotics.

The biomass-based encapsulating material used in the present invention uses biomass with promoting action to enzyme activity, for example, a polyphenol biomass-based material can be coordinated with a digestive enzyme, such that the enzyme activity is improved. By means of the coordinating effect, the armor (the first layer of nano-film) herein is further externally coated with a layer of digestive enzyme. These enzymes as protein shells can enhance the biocompatibility of the probiotics in the intestinal tract and under the promoting action of the first layer of encapsulating material, can keep very high enzyme activity, hydrolyze macromolecular nutritional substances quickly to promote the patient with intestinal dysfunction to absorb nutrition, and provide nutrition to the probiotics to promote fixed planting of the probiotics in the intestinal track and accelerate recovery of intestinal flora balance of the patient. In a complex external environment, for example, in the presence of active oxygen free radicals, the internal biomass-based armor can consume harmful substances nearby by adsorption, such that the enzyme activity is further maintained while the activity of the probiotics is maintained. The two layers of used encapsulating materials are bonded by multiple interactions such as π-π piling, hydrogen bonds, hydrophilic and lyophobic interactions and electrostatic interaction, are relatively high in bonding ability, are hard to dissociate and can protect the probiotics in a relatively long time. Meanwhile, the two layers of materials has hydrophilic and lyophobic properties, and water will form a layer of water nano-film on the surface of the material, such that sharp ice crystals can be prevented from being formed when the material is frozen. When a probiotics preparation generated by the encapsulated probiotics of the present invention is subjected to freeze drying, it is unnecessary to add a protecting agent, such that the probiotics can be prevented from being damaged in the freezing process extremely, and the activity of the probiotics is maintained.

The nano-film formed on the surfaces of the bacteria in situ by the biomass-based encapsulating material for protection of probiotic activity can be bonded with water molecules nearby, and formation of ice crystals can be avoided when the material is frozen, such that damage to the probiotics in the freezing process is avoided. The encapsulating method for the biomass-based encapsulating material for protection of probiotic activity is provided. The method is quite simple and fast, thereby facilitating implementation of low cost industrial production. A material for coating is the natural biological material which is very high in safety. The obtained probiotics preparation can maintain very high activity in transportation and storage processes, and therefore, the encapsulating method is suitable for the field of probiotics preparations.

The invention claimed is:

1. An encapsulated probiotic comprising:
a probiotics solution, wherein the probiotics solution has a concentration between $1*10^6$ CFU/mL and $1*10^9$ CFU/mL;
a biomass-based encapsulating material for protection of probiotic activity of the probiotics solution, the biomass-based encapsulating material comprising a nano-film, the nano-film comprising:
a first layer formed from covalent cross-linking or metal chelating action in situ between metal ions of a metal salt aqueous solution and biological macromolecules of a macromolecular aqueous solution, wherein the metal ions are selected from the group consisting of cations of Al, Fe, Zn, Mn, Ni, Co and V and combinations thereof, wherein the biological macromolecules are selected from the group consisting of polyphenol, dopamine, dopamine derivatives, polysaccharide biomass, and combinations thereof, wherein the metal salt aqueous solution has a concentration between 1 mg/mL and 10 mg/mL, wherein a volume ratio of the metal salt aqueous solution to the probiotics solution is 1:50, wherein the macromolecular aqueous solution has a concentration between 10 mg/mL and 100 mg/mL, wherein a volume ratio of the macromolecular aqueous solution to the probiotics solution is 1:50; and
a second layer formed by interactions between bio-enzymes of a bio-enzyme solution and the biological macromolecules of the macromolecular aqueous solution, wherein the bio-enzymes are selected from the group consisting of β-galactosidase, amylopsin, α-glucosaccharase, β-glucosaccharase, pancreatic lipase, trypsin, cellulose, and combinations thereof, wherein the bio-enzyme solution has a concentration between 1 mg/mL and 20 mg/mL, wherein a volume ratio of the bio-enzyme aqueous solution to the probiotics solution is 1:50.

2. The encapsulated probiotic according to claim 1, wherein the probiotics are one of or a mixture of two or more of lactic acid *bacillus, bacillus*, saccharomycetes, *bifidobacterium*, Gram-positive cocci, *Escherichia coli* and photosynthetic bacteria at any proportion.

3. The encapsulated probiotic according to claim 1, wherein when the first layer is formed from metal chelating action, the metal ions are complexed with catechol or carboxyl with the biological macromolecules.

4. The encapsulated probiotic according to claim 1, wherein when the first layer is formed from covalent cross-linking, catechol is crosslinked on the surfaces of cell walls of probiotics of the probiotics solution.

5. An encapsulating layer, comprising a nano-film for encapsulating probiotics, the nano-film comprising two layers, wherein a first layer is formed through biological macromolecules and metal ions on surfaces of the cell walls of probiotics of the probiotics solution by either covalent cross-linking or metal chelating action in situ, and a second layer is formed by interactions between a bio-enzyme and the biological macromolecules;
wherein the bio-enzyme is selected from the group consisting of β-galactosidase, amylopsin, α-glucosaccharase, β-glucosaccharase, pancreatic lipase, trypsin, cellulase and combinations thereof; wherein the metal ions are selected from the group consisting of cations of Al, Fe, Zn, Mn, Ni, Co, V, and combinations thereof;

wherein the biological molecules are selected from the group consisting of polyphenol, dopamine, dopamine derivatives, polysaccharide biomass at any proportion, and combinations thereof.

6. A method of encapsulating probiotics, comprising the following steps:

Step S1, mixing a metal salt aqueous solution with a probiotics solution fully, adding a biological macromolecular aqueous solution, adjusting a pH value, and carrying out washing to obtain a probiotics solution containing the probiotics coated with a first layer of a nano-film wherein a concentration of the probiotics solution obtained is $1*10^6$-$1*10^9$ CFU/mL, a concentration of the metal salt aqueous solution is 1-10 mg/mL, a concentration of the biological macromolecular aqueous solution is 10-100 mg/mL, a volume ratio of the metal salt aqueous solution to the probiotics solution is 1:50, and a volume ratio of the biological macromolecular aqueous solution to the probiotics solution obtained in the step S1 is 1:50;

Step S2, adjusting the concentration of the probiotics solution containing the probiotics coated by the first layer of the nano-film obtained in the step S1, and repeatedly operating the step S1 for 0-N times; and Step S3, adjusting the concentration of the probiotics solution containing the probiotics coated by the first layer of the nano-film obtained in the step S2, adding a bio-enzyme aqueous solution, to form the probiotics coated with the second layer of the nano-film, and carrying out freeze drying to obtain the encapsulated probiotics;

wherein the concentration of the probiotics solution containing the probiotics coated with the first layer of the nano-film after adjustment in the steps S2 and S3 is $1*10^6$-$1*10^9$ CFU/mL, a concentration of the bio-enzyme aqueous solution in the step S3 is 1-20 mg/mL, and a volume ratio of the bio-enzyme aqueous solution to the probiotics solution containing the probiotics coated with the first layer of the nano-film is 1:50, wherein the first layer is formed from covalent cross-linking or metal chelating action in situ between metal ions of the metal salt aqueous solution and biological macromolecules of the macromolecular aqueous solution, wherein the metal ions are selected from the group consisting of cations of Al, Fe, Zn, Mn, Ni, Co and V and combinations thereof, wherein the biological macromolecules are selected from the group consisting of polyphenol, dopamine, dopamine derivatives, polysaccharide biomass, and combinations thereof, and wherein the bio-enzymes of the bio-enzyme aqueous solution are selected from the group consisting of β-galactosidase, amylopsin, α-glucosaccharase, β-glucosaccharase, pancreatic lipase, trypsin, cellulose, and combinations thereof.

7. The method of encapsulating probiotics according to claim 6, wherein the pH is adjusted to 7.0 in the step S1 by adopting a sodium hydroxide aqueous solution or a PBS buffer solution.

8. The method of encapsulating probiotics according to claim 6, wherein a washing process in the step S1 comprises the following sub-steps: adding a PBS buffer solution into a mixed solution, and carrying out centrifugalization after full mixing to remove a supernate; repeating the operation for 1-3 times; and carrying out centrifugalization for 2-5 min by adopting a 1000-5000 g centrifugal force.

* * * * *